United States Patent
Cai et al.

(10) Patent No.: US 6,723,332 B2
(45) Date of Patent: Apr. 20, 2004

(54) OXOMIDAZOPYRIDINE-CARBOXAMIDES

(75) Inventors: Guolin Cai, Newbury Park, CA (US); Pamela A. Albaugh, Carmel, IN (US); Kenneth Shaw, Weston, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/864,846

(22) Filed: May 24, 2001

(65) Prior Publication Data

US 2002/0035120 A1 Mar. 21, 2002

Related U.S. Application Data

(60) Provisional application No. 60/209,855, filed on May 26, 2000.

(51) Int. Cl.[7] ..................... A01N 25/34; C07D 471/02; A61K 31/44
(52) U.S. Cl. ......................... 424/412; 546/123; 514/300
(58) Field of Search ................................ 546/123, 121; 514/300; 424/412

(56) References Cited

FOREIGN PATENT DOCUMENTS

| EP | 0 050 563 A | 4/1982 |
|---|---|---|
| WO | WO 97/26243 | 7/1997 |
| WO | WO 97/34870 | 9/1997 |
| WO | WO 98/02420 | 1/1998 |
| WO | WO 99/18105 | 4/1999 |
| WO | WO 99/37303 | 7/1999 |
| WO | WO 99/47131 | 9/1999 |
| WO | WO 99/47142 | 9/1999 |
| WO | WO 99/47171 | 9/1999 |
| WO | WO 01/16103 | 3/2001 |

OTHER PUBLICATIONS

Giuseppe, Trapani et al., "Synthesis and Binding Affinity of 2–Phenylimidazo '1,2lpyridine Derivatives for both Central and Peripheral Benzodiazepine Receptors. A New Series of High–Afinity and selective Ligands for the Peripheral Type", *J. Medicinal Chemistry*, vol. 40, No. 19, 1997, pp. 3109–3118.

Barnard, E.A. et al., International Union of Pharmacology. XV. Subtypes of gamma–Aminobutyric AcidA Receptors: Classification on the Basis of Subunit Structure and Receptor Function:, *Pharmacological Reviews*, vol. 50, No. 2, 1998, pp. 291–313.

*Primary Examiner*—Alan L. Rotman
*Assistant Examiner*—Binta Robinson
(74) *Attorney, Agent, or Firm*—McDonnell Boehnen Hulbert & Berghoff

(57) ABSTRACT

Disclosed are compounds of the formula:

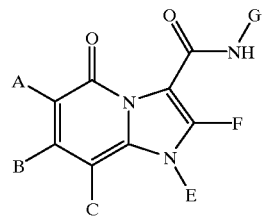

wherein:

A, B, C, E, F, and G are substituents as defined herein, which compounds bind to the benzodiazepine site of $GABA_A$ receptors and are therefore useful in treatment of central nervous system (CNS) diseases.

39 Claims, No Drawings

OXOMIDAZOPYRIDINE-CARBOXAMIDES

This application claims priority from U.S. Provisional Application Ser. No. 60/209,855, filed May 26, 2000, the disclosure of which is incorporated herein in its entirety.

BACKGROUND OF THE INVENTION

1. Field of the Invention

This invention relates to oxo-imidazopyridine-carboxamides that bind with high selectively and high affinity to the benzodiazepine site of $GABA_A$ receptors. This invention also relates to pharmaceutical compositions comprising such compounds and to the use of such compounds in treatment of central nervous system (CNS) diseases.

2. Description of the Related Art

The $GABA_A$ receptor super-family represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization. In addition to being the site of neurotransmitter action, a number of drugs including the anxiolytic and sedating benzodiazepines bind to this receptor. The $GABA_A$ receptor comprises a chloride channel that generally, but not invariably, opens in response to GABA, allowing chloride to enter the cell. This, in turn, effects a slowing of neuronal activity through hyper-polarization of the cell membrane potential.

$GABA_A$ receptors are composed of five protein subunits. A number of cDNAs for these $GABA_A$ receptor subunits have been cloned and their primary structures determined. While these subunits share a basic motif of 4 membrane-spanning helices, there is sufficient sequence diversity to classify them into several groups. To date at least 6α, 3β, 3γ, 1ε, 1δ and 2ρ subunits have been identified. Native $GABA_A$ receptors are typically composed of 2α, 2β, and 1γ subunits (Pritchett & Seeburg *Science* 1989; 245:1389–1392, and Knight et. al., Recept. *Channels* 1998; 6:1–18). Various lines of evidence (such as message distribution, genome localization and biochemical study results) suggest that the major naturally occurring receptor combinations are $α_1β_2γ_2$, $α_2β_3γ_2$, $α_3β_3γ_2$, and $α_5β_3γ_2$ (Mohler et al. *Neuroch. Res.* 1995; 20(5):631–36).

The $GABA_A$ receptor binding sites for GABA (2 per receptor complex) are formed by amino acids from the α and β subunits. Amino acids from the α and γ subunits together form 1 benzodiazepine site per receptor. Benzodiazepines exert their pharmacological actions by interacting with the benzodiazepine binding sites associated with the $GABA_A$ receptor. In addition to the benzodiazepine site (sometimes referred to as the benzodiazepine or BDZ receptor), the $GABA_A$ receptor contains sites of interaction for several other classes of drugs. These include a steroid binding site, a picrotoxin site, and a barbiturate site. The benzodiazepine site of the $GABA_A$ receptor is a distinct site on the receptor complex that does not overlap with the site of interaction for other classes of drugs that bind to the receptor or for GABA (see, e.g., Cooper, et al., The Biochemical Basis of Neuropharmacology, 6$^{th}$ ed., 1991, pp. 145–148, Oxford University Press, New York).

In a classic allosteric mechanism, the binding of a drug to the benzodiazepine site increases the affinity of the GABA receptor for GABA. Benzodiazepines and related drugs that enhance the ability of GABA to open $GABA_A$ receptor channels are known as agonists or partial agonists depending on the level of GABA enhancement. Other classes of drugs, such as β-carboline derivatives, that occupy the same site and negatively modulate the action of GABA are called inverse agonists. A third class of compounds exists. These compounds occupy the same site as both the agonists and inverse agonists and yet have little or no effect on GABA activity. These compounds will, however, block the action of agonists or inverse agonists and are thus referred to as $GABA_A$ receptor antagonists.

The important allosteric modulatory effects of drugs acting at the benzodiazepine site were recognized early, and the distribution of activities at different subtype receptors has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have enjoyed long pharmaceutical use as anxiolytics, these compounds are known to exhibit a number of unwanted side effects. These include cognitive impairment, sedation, ataxia, potentiation of ethanol effects, and a tendency for tolerance and drug dependence.

$GABA_A$ selective ligands also act to potentiate the effects of certain other CNS active compounds. For example, there is evidence that selective serotonin reuptake inhibitors (SSRIs) display greater antidepressant activity when used in combination with $GABA_A$ selective ligands than when used alone.

SUMMARY OF THE INVENTION

This invention provides oxo-imidazopyridine-carboxamide derivatives that bind with high affinity and high selectivity to the benzodiazepine site of $GABA_A$ receptors, including human $GABA_A$ receptors. Compounds of the invention bind, preferably with high selectivity and affinity, to $GABA_A$ receptors and thereby act as agonists, antagonists or inverse agonists of such receptors. As such, they are useful in the treatment of various CNS disorders.

The compounds of the invention bind with high selectivity and high affinity to the benzodiazepine site of $GABA_A$ receptors.

The invention provides compounds of Formula I (shown below), and pharmaceutical compositions comprising compounds of Formula I.

The invention further comprises methods of treating patients suffering from certain CNS disorders with an effective amount of a compound of the invention. The patient may be a human or other mammal. Treatment of humans, domesticated companion animals (pets) or livestock animals suffering from certain CNS disorders with an effective amount of a compound of the invention is encompassed by the invention.

In a separate aspect, the invention provides a method of potentiating the actions of other CNS active compounds. This method comprises administering an effective amount of a compound of the invention in conjunction with the administration of another CNS active compound.

In another, aspect this invention relates to the use of compounds of Formula I as probes for the localization of $GABA_A$ receptors in tissue sections. Such probes may be used in vitro (e.g., in binding assays) or in vivo (e.g., in PET or SPECT Scans).

Accordingly, in a broad aspect, the invention is directed to compounds of Formula I

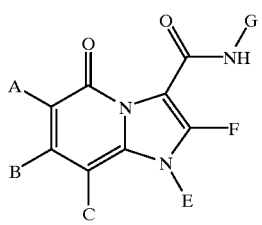

I and the pharmaceutically acceptable non-toxic salts thereof wherein:

A, B and C independently represent hydrogen, halogen, $C_1$–$C_6$ alkyl, wherein said $C_1$–$C_6$ alkyl is straight, branched or cyclic, contains zero, one or two double or triple bonds, and is unsubstituted or substituted with one or more substituents selected from hydroxy, oxo, halogen, amino, mono- or di($C_1$–$C_6$)alkylamino, $C_1$–$C_3$ alkoxy, and $C_3$–$C_7$ cycloalkyl, $C_1$–$C_6$ alkoxy, $C_1$–$C_6$ haloalkyl, hydroxy, amino, mono- or di($C_1$–$C_6$)alkylamino, $C_3$–$C_7$ cycloalkyl, mono- or di($C_1$–$C_6$)alkylamino ($C_1$–$C_6$) alkyl, mono- or di($C_1$–$C_6$) alkylamino ($C_1$–$C_6$)alkoxy, aryl($C_1$–$C_6$)alkyl and substituted aryl($C_1$–$C_6$)alkyl;

E is selected from hydrogen, hydroxy, $C_1$–$C_6$alkyl, and $C_1$–$C_6$ mono- or di($C_1$–$C_6$)alkyl amino($C_1$–$C_6$)alkyl;

F is selected from hydrogen, halogen, hydroxy, amino, and $C_1$–$C_6$ alkyl;

G is selected from aryl and heteroaryl, each of which is optionally substituted with up to three groups independently selected from the group consisting of halogen, $C_1$–$C_6$ alkyl, $C_1$–$C_6$ alkoxy, $C_1$–$C_6$ haloalkyl, hydroxy, mono- or di($C_1$–$C_6$)alkylamino, and $C_1$–$C_6$ alkyl substituted with one or two groups independently selected from —$OR^2$, —$NR^6R^7$, and heterocycloalkyl, where $R^2$, $R^6$ and $R^7$ are the same or different and represent hydrogen, $C_1$–$C_6$ alkyl, or $C_3$–$C_7$ cycloalkyl, or $NR^6R^7$ represents a cyclic moiety having 3–7 members.

In another aspect, the invention provides intermediates useful for preparing the compounds of Formula I.

In a further aspect, the invention provides methods for making compounds of Formula I.

DETAILED DESCRIPTION OF THE INVENTION

The compounds encompassed by the invention are represented by general Formula I (set forth above). The invention includes the pharmaceutically acceptable salts of those compounds.

Preferred compounds of Formula I (hereinafter compounds of Formula IA) are those where A, B and C are independently chosen from (i) hydrogen, halogen, $C_1$–$C_6$ alkoxy, $C_1$–$C_6$ haloalkyl, hydroxy;

(ii) $C_1$–$C_6$ alkyl, $C_3$–$C_7$ cycloalkyl, $C_2$-$C_6$ alkenyl, or $C_2$–$C_6$ alkynyl, where each alkyl, cycloalkyl, alkenyl, or alkynyl is optionally substituted with one or more of hydroxy, oxo, halogen, amino, $C_1$–$C_6$ haloalkyl, $C_3$–$C_7$ cycloalkyl, $C_{1-3}$ alkoxy, or mono- or dialkylamino;

(iii) $R^3R^4N$— where $R^3$ and $R^4$ independently represent hydrogen, $C_1$–$C_6$ alkyl, amino ($C_1$–$C_6$)alkyl, ($C_1$–$C_6$)alkoxy ($C_1$–$C_6$)alkyl, or $C_3$–$C_7$ cycloalkyl; or $NR^3R^4$ represents heteroaryl or heterocycloalkyl;

E is hydrogen; or

E is $C_1$–$C_6$ alkyl, amino($C_1$–$C_6$)alkyl, mono or di($C_1$–$C_6$alkyl)amino($C_1$–$C_6$)alkyl, or $C_1$–$C_6$alkoxy ($C_1$–$C_6$)alkyl, each of which alkyl portion being unsubstituted or substituted with one or more of halogen, hydroxy, $C_3$–$C_7$ cycloalkyl, aryl, heterocycloalkyl, or heteroaryl;

F is selected from hydrogen, halogen, hydroxy, amino, and $C_1$–$C_6$ alkyl; and G is selected from:

(i) a group of the formula

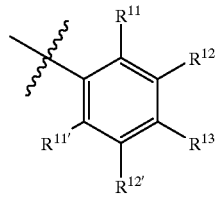

where $R^{11}$, $R^{11'}$, $R^{12}$, $R^{12'}$, and $R^{13}$ are the same or different and are selected from hydrogen, halogen, $C_1$–$C_6$ alkyl, hydroxy, trifluoromethyl, —$OR^2$, and —$NR^6R^7$ where $R^2$, $R^6$ and $R^7$ are the same or different and are selected from hydrogen, $C_1$–$C_6$ alkyl, and $C_3$–$C_7$ cycloalkyl; or $NR^6R^7$ represents aryl or heterocycloalkyl;

(ii) a group of the formula:

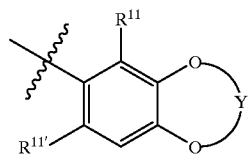

where Y is $C_1$–$C_6$ alkylene, and $R^{11}$ and $R^{11'}$ are as defined above;

(iii) a group of the formula:

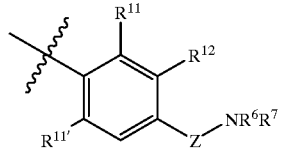

where $R^6$, $R^7$, $R^{11}$, and $R^{11'}$ are as defined above; and

Z is $C_1$–$C_6$alkylene or $C_1$–$C_6$alkyleneoxy;

(iv) a group of the formula:

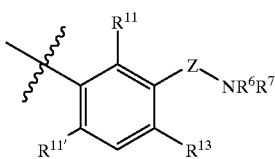

where Z, $R^6$, $R^7$, $R^{11}$, $R^{11'}$, and $R^{13}$ are as defined above;

(v) a group of the formula:

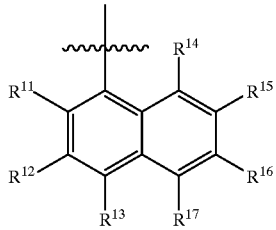

where $R^{11}$, $R^{12}$, and $R^{13}$ are as defined above, and $R^{14}$, $R^{15}$, $R^{16}$, and $R^{17}$ are the same or different and independently carry the same definition as $R^{11}$;

(vi) a group of the formula:

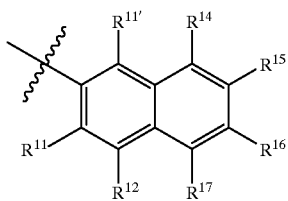

where $R^{11}$, $R^{11'}$, $R^{12}$, $R^{14}$, $R^{15}$, $R^{16}$, and $R^{17}$ are as defined above;

(vii) a group of the formula:

where Q represents a heteroaryl group.

In specific embodiments, Z is methylene, ethylene, methyleneoxy or ethyleneoxy.

The invention encompasses compounds of Formula III:

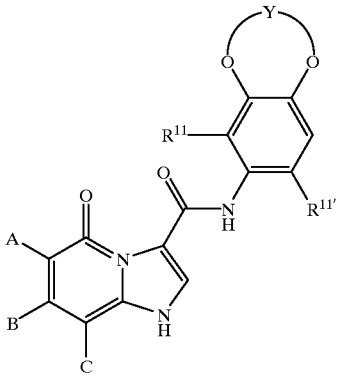

III where A, B, C, $R^{11}$, $R^{11'}$, and Y are as defined above for Formula IA.

Thus, the invention encompasses compounds of Formula II:

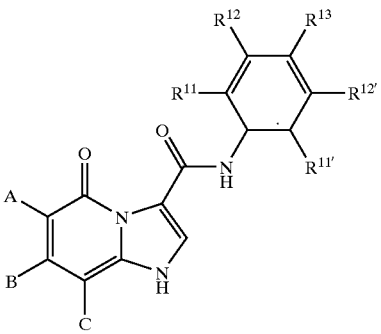

II where A, B, C, $R^{11}$, $R^{11'}$, $R^{12}$, $R^{12'}$ and $R^{13}$ are as defined above for Formula IA.

The invention encompasses compounds of Formula IV:

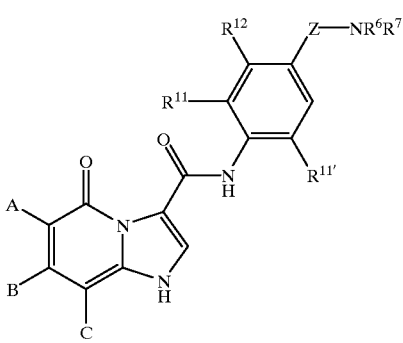

IV where A, B, C, $R^{11}$, $R^{11'}$, $R^{12}$, Z, $R^6$, and $R^7$ are as defined above for Formula IA.

The invention encompasses compounds of Formula V:

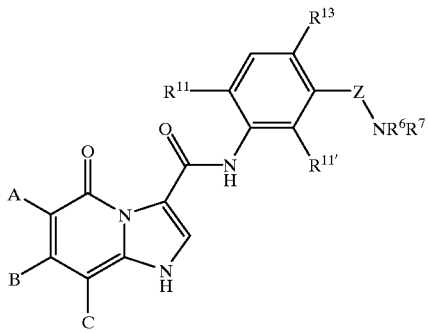

V where A, B, C, $R^{11}$, $R^{11'}$, $R^{13}$, Z, $R^6$, and $R^7$ are as defined above for Formula IA.

The invention encompasses compounds of Formula VI:

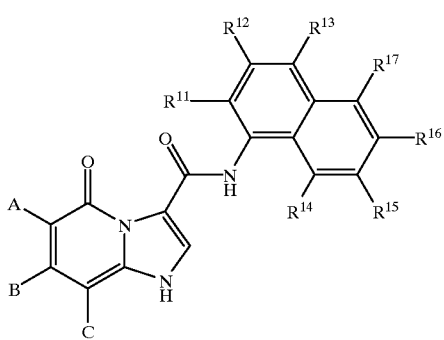

VI where A, B, C, $R^{11}$, $R^{12}$, $R^{13}$, $R^{14}$, $R^{15}$, $R^{16}$, and $R^{17}$ are as defined above for Formula IA.

The invention encompasses compounds of Formula VII:

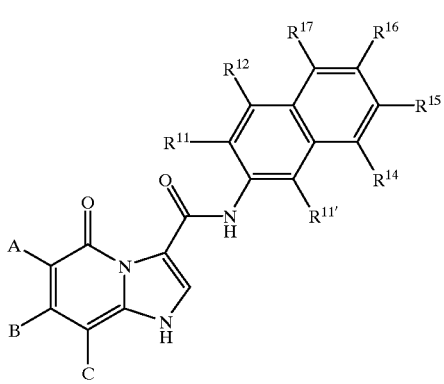

VII where A, B, C, $R^{11}$, $R^{12}$, $R^{11'}$, $R^{14}$, $R^{15}$, $R^{16}$, and $R^{17}$ are as defined above for Formula IA.

The invention encompasses compounds of Formula VIII:

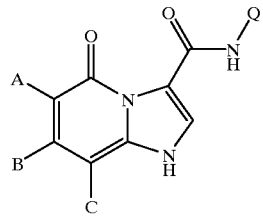

VIII where A, B and C are as defined above for Formula IA; and Q is heteroaryl.

The invention encompasses compounds of Formula IX:

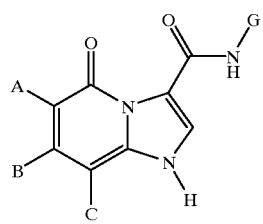

IX where A, B, C and G are as defined above for Formula IA.

The invention encompasses compounds of Formula X:

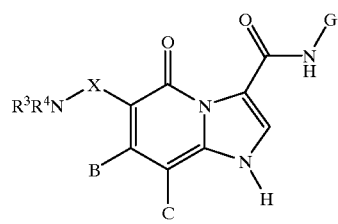

X where $R^3$, $R^4$, B, C, and G are as defined above for Formula IA, and X is $C_1$–$C_6$ alkylene.

The invention encompasses compounds of Formula XI:

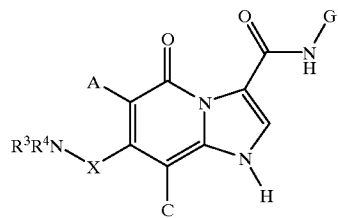

XI where A, C, G, $R^3$, and $R^4$ are as defined above for Formula IA, and X is $C_1$–$C_6$ alkylene.

The invention encompasses compounds of Formula XII:

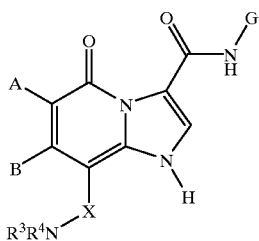

XII where A, B, G, $R^3$, and $R^4$ are as defined above for Formula IA, and X is $C_1$–$C_6$ alkylene.

The invention encompasses compounds of Formula XIII:

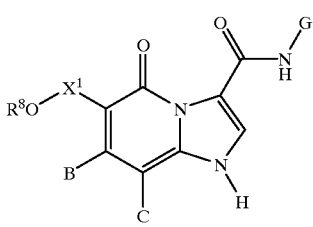

XIII where B, C, and G are as defined above for Formula IA, $R^8$ is defined the same as $R^2$, and $X^1$ is $C_1$–$C_6$alkylene or $C_1$–$C_6$ alkyleneamino.

The invention encompasses compounds of Formula XIV:

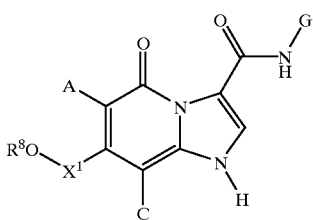

XIV where A, C, and G are as defined above for Formula IA, $R^8$ is defined the same as $R^2$, and $X^1$ is $C_1$–$C_6$alkylene or $C_1$–$C_6$ alkyleneamino The invention encompasses compounds of Formula XV:

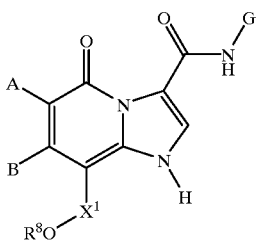

XV where A, B, and G are as defined above for Formula IA, $R^8$ is defined the same as $R^2$, and $X^1$ is $C_1$–$C_6$alkylene or $C_1$–$C_6$ alkylene amino.

The invention encompasses compounds of formula XVI:

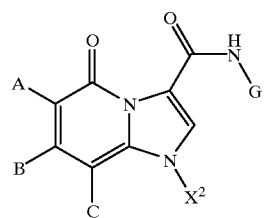

XVI where A, B, C, and G, $X^2$ is $C_1$–$C_6$alkyl.

The invention encompasses compounds of Formula XVII:

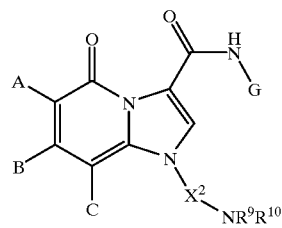

XVII where A, B, C, and G are as defined above for Formula IA, and $R^9$ and $R^{10}$ are defined the same as $R^3$ and $R^4$, and $X^2$ is $C_1$–$C_6$alkylene.

The invention encompasses compounds of Formula XVIII:

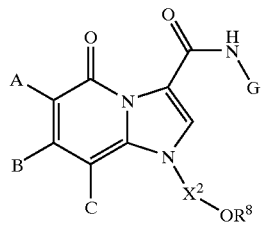

XVIII where A, B, C, and G are as defined above for Formula IA, and $R^8$ is defined the same as $R^2$, and $X^2$ is $C_1$–$C_6$alkylene.

Specific X groups are methylene and ethylene groups. Specific $X^1$ groups are methylene, ethylene, methyleneamino and ethyleneamino groups.

Preferred compounds of general Formula I are those where G is the group:

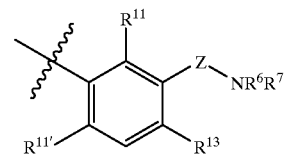

Z is alkyleneoxy or alkylene; and $NR^6R^7$ represents a 5- or 6-membered heteroaryl ring. Such preferred compounds are hereinafter referred to as compounds of Formula IB. Particularly preferred compounds of Formula IB are those where the 5- or 6-membered heteroaryl ring is imidazole, triazole, or pyrazole.

Other preferred compounds of Formula I are those of the formula:

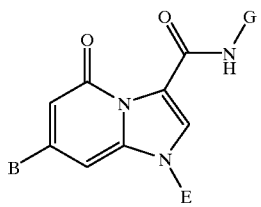

where
E and G are as defined above for Formula IA or for Formula IB; and
B is hydrogen or lower alkyl.

In this latter group of compounds, B is preferably hydrogen or $C_1$–$C_2$ alkyl, and most preferably hydrogen or methyl.

The invention further encompasses compounds of formula XIX

Formula XIX

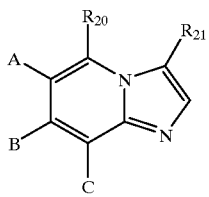

where
A, B and C are as defined for Formula I or IB;
$R_{20}$ represents halogen, $C_1$–$C_6$ alkoxy, or benzyloxy; and
$R_{21}$ represents hydrogen or halogen.

Particular compounds of Formula XIX are those where A and C are hydrogen, $R_{20}$ is halogen, preferably bromo, and $R_{21}$ is hydrogen. Other particular compounds of Formula XIX, are those where $R_{20}$ is $C_1$–$C_6$ alkoxy, preferably methoxy, and $R_{21}$ is hydrogen, or halogen. Still other particular compounds of Formula XIX, are those where A and C are hydrogen, $R_{20}$ is $C_1$–$C_6$ alkoxy, preferably methoxy, $R_{21}$ is halogen, preferably bromo, and B is $C_1$–$C_6$ alkyl.

The invention also encompasses compounds of Formula XX,

Formula XX

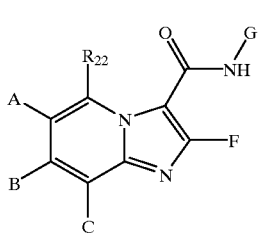

where
A, B, C, E, G and F carry the same definitions as for Formula I or IB; and $R_{22}$ represents benzyloxy or $C_1$–$C_6$ alkoxy, preferably methoxy.

Preferred compounds of Formula XX include those where B is $C_1$–$C_6$ alkyl, preferably $C_1$–$C_2$ alkyl, A, C, F, and E are hydrogen, and $R_{22}$ is $C_1$–$C_6$ alkyl, preferably $C_1$–$C_2$ alkyl, most preferably methyl.

In certain situations, compounds of Formula I may contain one or more asymmetric carbon atoms, so that the compounds can exist in different stereoisomeric forms. These compounds can be, for example, racemates or optically active forms. In these situations, the single enantiomers (optically active forms) can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds set forth in Table I and their pharmaceutically acceptable acid and base addition salts. If the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitic, bencoic, citric, tartaric, maleic, hydroiodic, alkanoic such as acetic, HOOC—$(CH_2)n$—COOH where n is 0–4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

The present invention also encompasses the acylated prodrugs of the compounds of Formula I. Those skilled in the are will recognize various synthetic methodologies that may be employed to prepare non-toxic pharmaceutically acceptable addition salts and acylated prodrugs of the compounds encompassed by Formula I.

By "lower alkyl" and "$C_1$–$C_6$ alkyl" is meant straight or branched chain alkyl groups having the indicated number of carbon atoms when a number is indicated. Examples of such groups are methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "cycloalkyl" and "$C_3$–$C_7$ cycloalkyl" is meant cycloalkyl groups having 3–7 atoms such as, for example cyclopropyl, cyclobutyl, cyclopenyl, cyclohexyl, and cycloheptyl.

By "aryl" is meant an aromatic carbocyclic group having a single ring (e. g., phenyl), multiple rings (e. g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, $C_1$–$C_6$ haloalkyl, hydroxy, or mono- or di-($C_1$–$C_6$) alkylamino.

In the term "substituted aryl($C_1$–$C_6$)alkyl", it is understood that the aryl group is substituted as provided in the preceding paragraph, i.e., one, two, or three substituents selected from, e.g., halogen, lower alkyl, lower alkoxy, $C_1$–$C_6$ haloalkyl, hydroxy, and mono- or di-($C_1$–$C_6$) alkylamino.

By "lower alkoxy" is meant straight or branched chain alkoxy groups having 1–6 carbon atoms, such as, for example, methoxy, ethoxy, propoxy, isopropoxy, n-botoxy, sec-butoxy, tert-butoxy, pentoxy, 2-pentyl, isopentoxy, neopentoxy, hexoxy, 2-hexoxy, and 3-methylpentoxy.

By "halogen" is meant fluorine, bromine, chlorine, and iodine.

By "haloalkyl" as used herein is meant $C_1$–$C_6$ alkyl groups where one or more hydrogen atoms is replaced by a halogen atom. Representative examples include fluoromethyl, difluoromethyl, cloromethyl, bromomethyl, 1,2-difluoroethyl, trifluoromethyl, perfluoropropyl, 2,2-dichloropropyl, etc. A preferred haloalkyl group is trifluoromethyl.

By "heteroaryl" or "aromatic heterocycle" is meant one or more aromatic ring systems of 5-, 6-, or 7-membered rings containing at least one and up to four hetero atoms selected from nitrogen, oxygen, or sulfur. Such heteroaryl groups include but are not limited to thienyl, furanyl, thiazolyl, imidazolyl, (is)oxazolyl, pyridyl, pyrimidinyl, (iso)quinolinyl, naphthyridinyl, benzimidazolyl, and benzoxazolyl heterocyclic groups. These heteroaryl groups may be unsubstituted or substituted in a substitutable position with one or more groups selected independently from halogen, hydroxy, $C_1$–$C_6$ alkyl, $C_1$–$C_6$ alkoxy, $C_1$–$C_6$ haloalkyl, and mono- or di ($C_1$–$C_6$)alkylamino.

Specific examples of heteroaryl groups include:

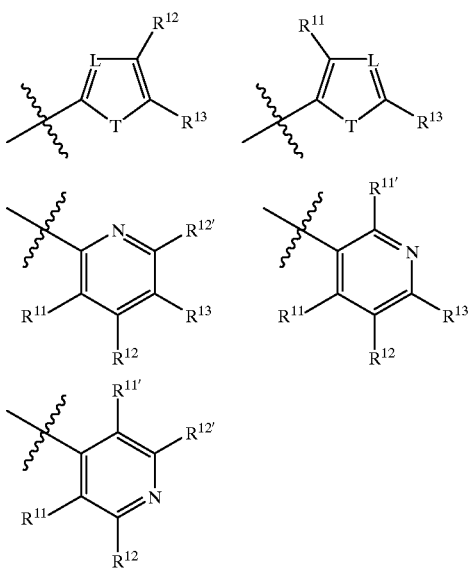

wherein
L is nitrogen or —$CR^{11}$;
T is —$NR^{19}$, oxygen, or sulfur;
$R^{11}$, $R^{12}$, $R^{13}$, $R^{11'}$, and $R^{12'}$ are as defined above; and
$R^{19}$ is hydrogen or $C_1$–$C_6$alkyl.

By "heterocycloalkyl" or "heterocyclic ring" is meant saturated or partially unsaturated ring structures having from 3 to about 8 ring atoms, with at least one ring atom selected from nitrogen, oxygen, and sulfur and remaining ring atoms being carbon. Heterocyclic rings may be unsubstituted or substituted with one or more groups such as halogen, hydroxy, $C_1$–$C_6$ haloalkyl, $C_1$–$C_6$ alkyl, $C_1$–$C_6$ alkoxy, amino, or mono or di($C_1$–$C_6$)alkylamino. Examples of such rings are piperidinyl, piperazinyl, morpholinyl, pyrrolidinyl, imidazolinyl, homopiperazinyl, and homopiperidinyl.

In terms such as di($C_1$–$C_6$)alkylamino, di($C_1$–$C_6$) alkylamino ($C_1$–$C_6$) alkyl, and di($C_1$–$C_6$) alkylamino ($C_1$–$C_6$) alkoxy, it is understood that the selection of each alkyl portion is independent of any other alkyl portion in the group. Thus, for example, di($C_1$–$C_6$)alkylamino includes N-methyl-N-propylamino, N-ethyl-N-butylamino, N-methyl-N-ethylamino, etc.

The definition of Formula I as shown in the specification and as used in the claims includes possible isomers, such as tautomers and rotamers. The Formulas IIc and IId, below, illustrate this point.

For Formula I, when E=H:

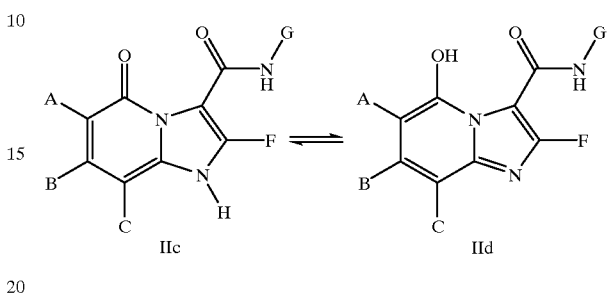

IIc            IId

The following numbering system is used to identify positions on the imidazopyridole ring system of the compounds of the invention:

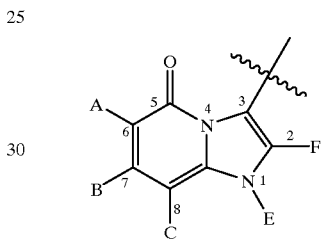

Representative compounds of the invention are shown in Table I.

TABLE I

Compound A

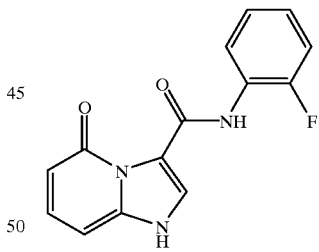

Compound B

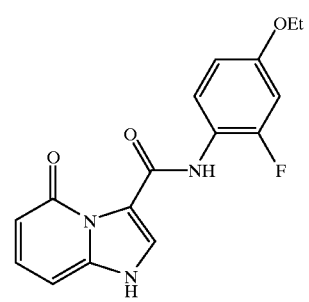

Compound C

TABLE I-continued

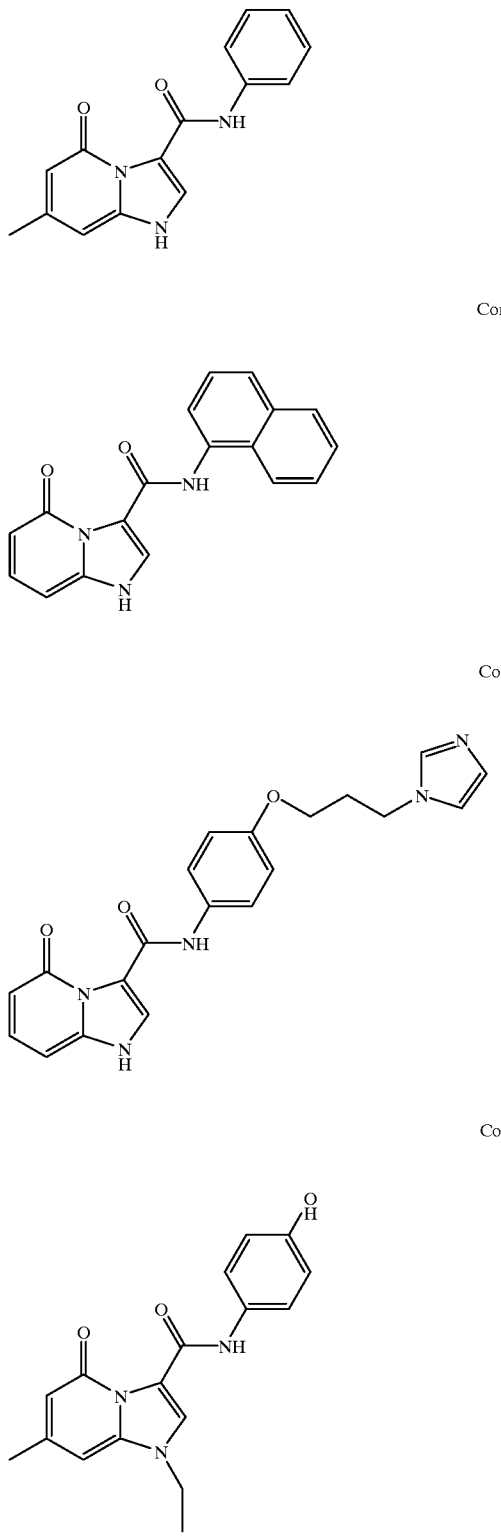

Compound D

Compound E

Compound F

Compound G

TABLE I-continued

Compound H

The compounds of the invention interact with a GABA binding site, the benzodiazepine (BDZ) receptor, as shown in the examples.

This invention provides oxo-imidazopyridine carboxamides that bind, preferably with high affinity, to the benzodiazepine site of $GABA_A$ receptors, including human $GABA_A$ receptors. Preferred compounds are those that show high selectivity for the benzodiazepine site of GABAa receptors.

The compounds of Formula I and their salts are suitable for the diagnosis and treatment of anxiety, depression, memory impairment, Alzheimer's dementia, Down Syndrome, sleep, cognitive and seizure disorders, and overdose with benzodiazepine drugs and for enhancement of alertness, both in human and non-human animals including companion animals, e.g. domestic pets, especially dogs and cats and livestock animals, e.g., sheep, swine and cattle.

The diseases and/or disorders that can be treated using compounds and compositions according to the invention include:

Depression:
    depression, atypical depression, bipolar disorder, depressed phase of bipolar disorder.

Anxiety:
    general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclopthymia Sleep Disorders:
sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder Cognition impairment:
cognition impairment, Alzheimer's disease, Parkinson's disease, mild cognitive impairment (MCI), age-related cognitive decline (ARCD), stroke, traumatic brain injury, AIDS associate dementia, dementia associated with depression, anxiety or psychosis The invention also provides pharmaceutical compositions comprising compounds of the invention.

The invention further comprises methods of treating patients in need of such treatment with an amount of a compound of the invention sufficient to alter the symptoms of a CNS disorder. Compounds of the inventions that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; as well as stress disorders, including post-traumatic stress and acute stress disorders. Compounds of the inventions that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at an $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at a $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

In a separate aspect, the invention provides a method of potentiating the actions of CNS active compounds that comprises administering an effective amount of a compound of the invention in combination with another CNS active compound. Such CNS active compounds include, but are not limited to the following: for anxiety, serotonin receptor (e.g. 5-HT$_{1A}$) agonists and antagonists; for anxiety and depression, neurokinin receptor antagonists or corticotropin releasing factor receptor (CRF$_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. In a preferred embodiment, the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that described by disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the GABA$_A$ receptor ligand 3-(5-methylisoxazol-3-yl)-6-(1-methyl-1,2,3-triazol-4-yl) methyloxy-1,2,4-triazolo [3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of GABA$_A$ receptor ligands, 1,2,4-triazolo[4,3-b]pyridazines, in combination with SSRIs.

The present invention also pertains to methods of inhibiting the binding of benzodiazepine compounds, such as Ro15-1788, to GABA$_A$ receptors which methods involve contacting a compound of the invention with cells expressing GABA$_A$ receptors, wherein the compound is present at a concentration sufficient to inhibit benzodiazepine binding to GABA$_A$ receptors in vitro. This method includes inhibiting the binding of benzodiazepine compounds to GABA$_A$ receptors in vivo, e.g., in a patient given an amount of a compound of Formula I that would be sufficient to inhibit the binding of benzodiazepine compounds to GABA$_A$ receptors in vitro. In one embodiment, such methods are useful in treating benzodiazepine drug overdose. The amount of a compound that would be sufficient to inhibit the binding of a benzodiazepine compound to the GABA$_A$ receptor may be readily determined via an GABA$_A$ receptor binding assay, such as the assay described in Example 9. The GABA$_A$ receptors used to determine in vitro binding may be obtained from a variety of sources, such as, for example, from preparations of rat cortex or from cells expressing cloned human GABA$_A$ receptors.

The present invention also pertains to methods for altering the signal-transducing activity, particulary the chloride ion conductance of GABA$_A$ receptors, said method comprising exposing cells expressing such receptors to an effective amount of a compound of the invention. This method includes altering the signal-transducing activity of GABA$_A$ receptors in vivo, e.g., in a patient given an amount of a compound of Formula I that would be sufficient to alter the signal-transducing activity of GABA$_A$ receptors in vitro. The amount of a compound that would be sufficient to alter the signal-transducing activity of GABA$_A$ receptors may be determined via a GABA$_A$ receptor signal transduction assay, such as the assay described in Example 10.

The GABA$_A$ receptor ligands provided by this invention and labeled derivatives thereof are also useful as standards and reagents in determining the ability of a potential pharmaceutical to bind to the GABA$_A$ receptor.

Labeled derivatives the GABA$_A$ receptor ligands provided by this invention are also useful as radiotracers for positron emission tomography (PET) imaging or for single photon emission computerized tomography (SPECT).

Additionally this invention relates to the use of compounds of Formula I as probes for the localization of GABA$_A$ receptors, e.g., in tissue sections.

Pharmaceutical Preparations

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula II may be present in association with one or more non-toxic pharmaceutically acceptable carriers and/or diluents and/or adjuvants and if desired other active ingredients. The pharmaceutical compositions containing compounds of general Formula II may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques so as to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the drug or a pharmaceutical composition containing the drug may also be added to animal feed or drinking water. It will be convenient to formulate animal feed and drinking water products with a predetermined dose of the drug so that the animal takes in an appropriate quantity of the drug along with its diet. It will also be convenient to add a premix containing the drug to the feed or drinking water approximately immediately prior to consumption by the animal.

Preferred compounds of the invention have various pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat peripheral disorders are often preferred.

Assays may be used to predict these pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to GABA$_A$ receptor modulation, e.g., treatment of anxiety, depression, sleep disorders or cognitive impairment by GABA$_A$ receptor modulation. The packaged pharmaceutical compositions include a container holding a therapeutically effective amount of at least one GABA$_A$ receptor modulator as described herein and instructions (e.g., labeling) indicating the contained GABA$_A$ receptor ligand is to be used for treating a disorder responsive to GABA$_A$ receptor modulation in the patient.

An illustration of the preparation of compounds of the present invention is given in Scheme 1.

Scheme I:

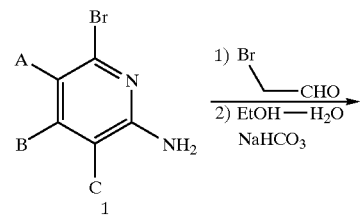

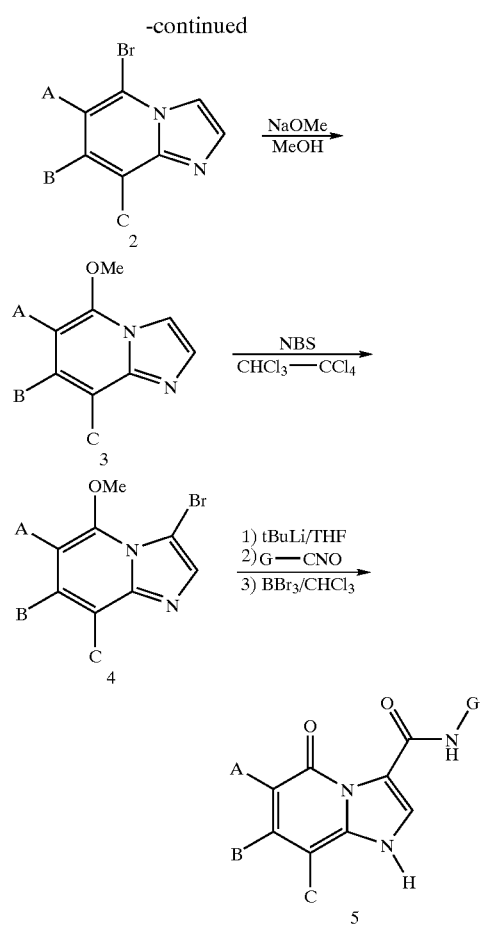

In Scheme I, the substituents A, B, B and G carry the definitions set forth above for Formula II.

The disclosures in this application of all articles and references, including patents, are incorporated herein by reference.

The invention is illustrated further by the following examples, which are not to be construed as limiting the invention in scope or spirit to the specific procedures described in them. Those having skill in the art will recognize that the starting materials and reaction conditions may be varied and additional steps employed to produce compounds encompassed by the present invention, as demonstrated by the following examples. Unless otherwise stated, the starting material and reagents employed in these syntheses are of standard commercial grade. In some cases, protection of certain reactive functionalities may be necessary to achieve some of the above transformations. In general, the need for protecting groups, as well as the conditions necessary to attach and remove such groups, will be apparent to those skilled in the art of organic synthesis.

Representative examples of methods for preparing compounds of the invention are set forth below.

EXAMPLE 1

Preparation of Starting Materials and Intermediate

The starting materials and various intermediates may be obtained from commercial sources, prepared from commercially available organic and/or inorganic reagents and compounds, or prepared using well known synthetic methods.

Representative examples of methods for preparing intermediates of the invention are set forth below.

Preparation of 5-bromo-7-methylimidazo[1,2-a]pyridine

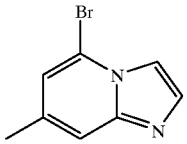

A mixture of bromoacetaldehyde diethyl acetal (20 mL), concentrated hydrobomic acid (5 mL) and water (20 mL) is heated at 90° C. for 1.5 h. The reaction mixture is poured into 250 mL of water and 50 g sodium bicarbonate is gradually added. 2-Amino-6-bromo-4-methylpyridine (3 g, 0.016 mol) is then added and the mixture is stirred at room temperature for 3 h. Ethyl acetate (100 mL) and water (50 mL) are added. The organic layer is separated and extracted with hydrochloric acid (1N, 3×100 mL). The combined aqueous layer is neutralized with ammonium hydroxide at 0° C. and extracted with dichloromethane (3×200 mL). The combined organic layer is dried over sodium sulfate. Evaporation of the solvent gave 5-bromo-7-methylimidazo[1,2-a]pyridine (2.95 g, 76%) as a white solid, m.p. 53–54° C.

EXAMPLE 2

Preparation of 5-methoxy-7-methylimidazo[1,2-a]pyridine

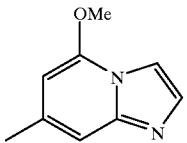

A solution of 5-bromo-7-methylimidazo[1,2-a]pyridine (2 g, 0.01 mol) and sodium methoxide (25%, 10 mL) in methanol (10 mL) is heated under reflux for 48 h. The solvent is removed and the residue diluted with ethyl acetate (200 mL) and water (150 mL). The organic layer is separated and washed with water and brine, and dried over sodium sulfate. Evaporation of the solvent gave 5-methoxy-7-methylimidazo[1,2-a]pyridine (lg, 62%) as a white semi-solid.

EXAMPLE 3

Preparation of 3-bromo-5-methoxy-7-methylimidazo[1,2-a]pyridine

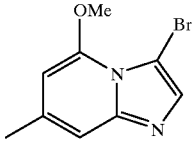

To a solution of 5-methoxy-7-methylimidazo[1,2-a]pyridine (900 mg, 5.6 mmol) in carbon tetrachloride (100 mL), is added N-bromosuccimide (990 mg, 5.6 mmol). It is stirred at room temperature for 2 h. The reaction solution is then filtered through celite and the filtrate concentrated in vacuo. Ethyl acetate (150 mL) and water are added to the residue. The organic layer is separated and extracted with hydrochloric acid (1N, 3×100). The combined aqueous layer is neutralized with ammonium hydroxide at 0° C. and extracted with dichloromethane (3×200 mL). The combined organic layer is dried over sodium sulfate. The solvent is removed to give 3-bromo-5-methoxy-7-methylimidazo[1,2-a]pyridine (1.1 g, 78%) as a white solid, m.p. 105–106° C.

EXAMPLE 4

Preparation of N-(2,5-fluorophenyl)5-methoxy-7-methylimidazo [1,2-a]pyridyl-3-carboxamide

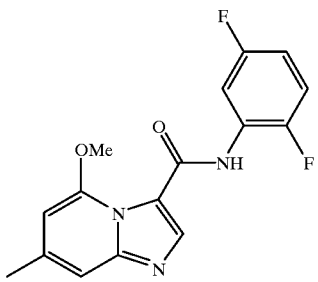

To a solution of 3-bromo-5-methoxy-imidazo[1,2-a]pyridine (400 mg, 17.5 mmol) in THF (20 mL) is added a solution of t-butyl lithium in pentane (1.5 M, 3 mL, 4.5 mmol) at −78° C. The resulting solution is stirred at −78° C. under Argon for 5 mins. and is then treated with 2,5-difluorophenyl isocyanate (0.3 mL) at −78° C. The solution is warmed to room temperature and stirred at room temperature for 30 mins. Ethyl acetate (15 mL) and water are added. The organic layer is separated and extracted with hydrochloric acid (1N, 3×15 mL). The combined aqueous layer is neutralized with ammonium hydroxide at 0° C. and extracted with dichloromethane (3×20 mL). The combined organic layer is dried over sodium sulfate. Evaporation of the solvent gives an oily residue, which is triturated with ether to give N-(2,5-fluorophenyl)5-methoxy-7-methylimidazo[1,2-a]pyridyl -3-carboxamide (302 mg, 57%) as a cream colored solid, m.p. 155–157° C.

EXAMPLE 5

Preparation of N-(2,5-difluorophenyl) 7-methyl-5-oxo-imidazo [1,2-a]pyridyl-3-carboxamide

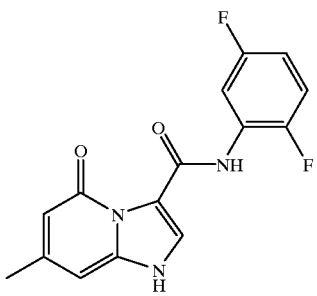

To a solution N-(2, 5-difluorophenyl)-5-methoxy-7-methylimidazo[1,2-a]pyridyl-3-carboxamide (110 mg, 0.36 mmol) in chloroform (10 mL) is added a solution of boron tribromide in dichloromethane (1.0 M, 2 ml, 2 mmol) dropwise at 0° C. The mixture is then stirred at room temperature for 3 h and quenched with methanol. Solvent is then removed in vacuo to dryness. Sodium bicarbonate saturated solution (20 mL) is added to the residue. The solid is filtered, rinsed with water, dichloromethane and dried to give 80 mg of solid product, which is recrystalized from ethanol, to give N-(2,5-difluorophenyl) 7-methyl-5-oxo-imidazo[1,2-a]pyridyl-3-carboxamide (Compound 1) as colorless solid. m.p. >285° C. (dec.).

EXAMPLE 6

The following compounds of Formula I are prepared essentially according to the procedures described in Examples 1–5:

TABLE II

| No. | B | E | G | Name | m.p.(° C.) |
|---|---|---|---|---|---|
| 2 | H | H | Phenyl | N-Phenyl 5-oxo-imidazo[1,2-a]pyridine-3-carboxamide | 244–246 |
| 3 | H | H | 2-Fluorophenyl | N-(2-Fluorophenyl)5-oxo imidazo[1,2-a]pyridine-3-carboxamide | 245–247 |
| 4 | H | H | 2-Fluoro-4-chlorophenyl | N-(2-fluoro 4-Chloro-phenyl) 5-oxo imidazo[1,2-a]pyridine-3-carboxamide | 215–220 |
| 5 | H | H | 2-Fluoro-3-trifluoromethyl-phenyl | N-(2-Fluoro-3-trifluoromethylphenyl)5-oxo-imidazo[1,2-a]pyridine-3-carboxamide | 274–277 (dec.) |
| 6 | H | H | 3-Methylphenyl | N-(3-Methylphenyl) 5-oxo-imidazo[1,2-a]pyridine-3-carboxamide | >283 (dec.) |
| 7 | H | H | 2-Fluoro-5-methylphenyl | N-(2-Fluoro-5-methylphenyl)5-oxo-imidazo[1,2-a]pyridine-3-carboxamide | 280–285 (dec.) |
| 8 | H | H | 4-Trifluoromethoxy-phenyl | N-(4-Trifluoromethoxyphenyl) 5-oxo-imidazo[1,2-a]pyridine-3-carboxamide | 273–275 |
| 9 | H | H | 2-Fluoro-4-ethoxyphenyl | N-(2-Fluoro-4-ethoxyphenyl)5-oxo-imidazo[1,2-a]pyridine-3-carboxamide | >216 (dec.) |
| 10 | H | H | 4-(2-Dimethylamino-ethoxy)phenyl | N-[4-(2-Dimethylaminoethoxy)phenyl]5-oxo-imidazo[1,2-a]pyridine-3-carboxamide | 198–210 |
| 11 | H | H | 4-(3-Imidazyl-1-propoxy)phenyl | N-[4-(3-Imidazyl-1-propoxy)phenyl]5-oxo-imidazo[1,2-a]pyridine-3-carboxamide hydrochloride | 210–216 |
| 12 | H | H | 2-Naphthyl | N-(2-Naphthyl)5-oxo-imidazo[1,2-a]pyridine-3-carboxamide | 259–265 |
| 13 | $CH_3$ | H | Phenyl | N-Phenyl 7-methyl 5-oxo-imidazo[1,2-a]pyridine-3-carboxamide | >275 (dec.) |
| 14 | $CH_3$ | H | 4-Fluorophenyl | N-(4-Fluorophenyl)7-methyl 5-oxo-imidazo[1,2-a]pyridine-3-carboxamide | >274 (dec.) |
| 15 | $CH_3$ | H | 4-Hydroxyphenyl | N-(4-Hydroxyphenyl)7-methyl 5-oxo-imidazo[1,2-a]pyridine-3-carboxamide | >250 (dec.) |
| 16 | $CH_3$ | H | 2,4-Difluorophenyl | N-(2,4-Difluorophenyl)7-methyl 5-oxo-imidazo[1,2-a]pyridine-3-carboxamide | 265–268 (dec.) |
| 17 | $CH_3$ | H | 2,5-Difluorophenyl | N-(2,5-Difluorophenyl)7-methyl 5-oxo-imidazo[1,2-a]pyridine-3-carboxamide | 284–286 (dec.) |

TABLE II-continued

[Structure: imidazo[1,2-a]pyridine-3-carboxamide core with substituents B (at 7-position), E (at N1), and G (on carboxamide N), with 5-oxo group]

| No. | B | E | G | Name | m.p.(° C.) |
|---|---|---|---|---|---|
| 18 | CH₃ | H | 2-Fluoro-4-hydroxyphenyl | N-(2-Fluoro-4-hydroxyphenyl)7-methyl 5-oxo-imidazo[1,2-a]pyridine-3-carboxamide | >242 (dec.) |
| 19 | CH₃ | CH₃CH₂— | 4-Hydroxyphenyl | N-(4-Hydroxyphenyl)1-(N-Ethyl)7-methyl 5-oxo-imidazo[1,2-a]pyridine-3-carboxamide. | |
| 20 | CH₃ | 3-imidazyl-1-propyl- | 4-Hydroxyphenyl | N-(4-Hydroxyphenyl)1-(3-imidazyl-1-propyl)-7-methyl 5-oxo-imidazo[1,2-a]pyridine-3-carboxamide | |

EXAMPLE 7

Preparation of Radio-Labeled Probe Compounds of the Invention

The compounds of the invention are prepared as radio-labeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radio-labeled probes are conveniently synthesized by a radioisotope supplier specializing in custom synthesis of radio-labeled probe compounds. Such suppliers include Amersham Corporation, Arlington Heights, Ill.; Cambridge Isotope Laboratories, Inc. Andover, Mass. SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radio-labeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 8
Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radio-labeled compounds of the invention prepared as described in the preceding Example.

EXAMPLE 9
Binding Assay

The following assay is a standard GABAa receptor binding assay. The high affinity and high selectivity of compounds of this invention for the benzodiazepine site of the $GABA_A$ receptor is shown using the binding assay described by Thomas and Tallman (*J. Bio. Chem.* 1981; 156:9838–9842, and *J. Neurosci.* 1983; 3:433–440). Essentially the same assay is described below.

Rat cortical tissue is dissected and homogenized in 25 volumes (w/v) of Buffer A (0.05 M Tris HCl buffer, pH, 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations contained 100 μl of tissue homogenate, 100 μl of radioligand, (0.5 nM $^{3}H$-Ro15-1788 [$^{3}H$-Flumazenil], specific activity 80 Ci/mmol), and test compound or control (see below), and are brought to a total volume of 500 μl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^{3}H$ Ro15-1788 with 10 mM Diazepam (Research Biochemicals International, Natick, Mass.). Data are collected in triplicate, averaged, and percent inhibition of total specific binding (Total Specific Binding=Total−Nonspecific) is calculated for each compound.

A competition binding curve is obtained with up to 11 points spanning the compound concentration range from $10^{-12}$ M to $10^{-5}$ M obtained per curve by the method described above for determining percent inhibition. $K_i$ values are calculated according the Cheng-Prussof equation. Each of the compounds set forth in Examples 5–6 as compounds 1 through 20 is tested in this fashion and each is found to have a $K_i$ of <1 μM. Preferred compounds of the invention exhibit $K_i$ values of less than 100 nM and more preferred compounds of the invention exhibit $K_i$ values of less than 10 nM.

EXAMPLE 10

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6:1313–1316, 1995) and White, Gurley, Hartnett, Stirling, and Gregory (Receptors and Channels 3:1–5, 1995) with modifications. Electrophysiological recordings are carried out using the two electrode voltage-clamp technique at a membrane holding potential of −70 mV. Xenopus Laevis oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 µM GABA is applied.

Compounds are evaluated against a GABA concentration that evokes <10% of the maximal evokable GABA current (e.g. 1 µM-9µM). Each oocyte is exposed to increasing concentrations of a compound being evaluated (test compound) in order to evaluate a concentration/effect relationship. Test compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a test compound for the benzodiazepine site is determined following completion of a concentration/effect curve. After washing the oocyte sufficiently to remove previously applied test compound, the oocyte is exposed to GABA+1 µM RO15-1788, followed by exposure to GABA+1 µM RO15-1788+test compound. Percent change due to addition of compound is calculated as described above. Any percent change observed in the presence of RO15-1788 is subtracted from the percent changes in current amplitude observed in the absence of 1 µM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

It is to be understood that the foregoing describes preferred embodiments of the present invention and that modifications may be made therein without departing from the spirit of scope of the present invention as set forth in the following claims.

What is claimed is:

1. A compound of the formula:

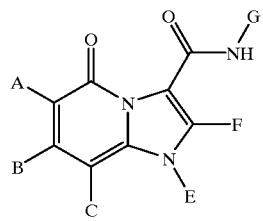

or a pharmaceutically acceptable salt thereof wherein:

A, B and C are independently selected from:
   (i) hydrogen, halogen, $C_1$–$C_6$ alkoxy, $C_1$–$C_6$ haloalkyl, hydroxy;
   (ii) $C_1$–$C_6$ alkyl, $C_3$–$C_7$ cycloalkyl, $C_2$–$C_6$ alkenyl, $C_2$–$C_6$ alkynyl,
      where each alkyl, cycloalkyl, alkenyl, or alkynyl is optionally substituted with one or more of hydroxy, oxo, halogen, amino, $C_1$–$C_6$ haloalkyl, $C_3$–$C_7$ cycloalkyl, $C_1$–$C_3$ alkoxy, or mono- or di($C_1$–$C_6$)alkylamino; and
   (iii) $R^3R^4N$— where
      $R^3$ and $R^4$ independently represent hydrogen, $C_1$–$C_6$ alkyl, amino($C_1$–$C_6$)alkyl, ($C_1$–$C_6$)alkoxy($C_1$–$C_6$) alkyl, or $C_3$–$C_7$ cycloalkyl; and E is hydrogen or E is $C_1$–$C_6$ alkyl, amino($C_1$–$C_6$)alkyl, mono or di($C_1$–$C_6$ alkyl)amino($C_1$–$C_6$)alkyl, or $C_1$–$C_6$alkoxy($C_1$–$C_6$) alkyl, each alkyl portion being unsubstituted or substituted with one or more of halogen, hydroxy, $C_3$–$C_7$ cycloalkyl, or aryl;

F is selected from hydrogen, halogen, hydroxy, amino, and $C_1$–$C_6$ alkyl;

G is selected from
   (i) a group of the formula

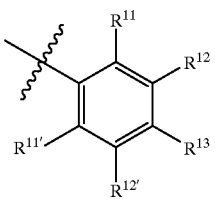

where $R^{11}$, $R^{11'}$, $R^{12}$, $R^{12'}$, and $R^{13}$ are the same or different and are selected from
      hydrogen, halogen, $C_1$–$C_6$ alkyl, hydroxy, trifluoromethyl,
      —$OR^2$, imidazyl ($C_2$–$C_4$)alkoxy, and —$NR^6R^7$, where $R^2$, $R^6$ and $R^7$ are the same or different and are selected from hydrogen, $C_1$–$C_6$ alkyl, and $C_3$–$C_7$ cycloalkyl;

(iii) a group of the formula:

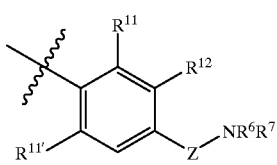

where $R^6$, $R^7$, $R^{11}$, and $R^{11'}$ are as defined above; and Z is $C_1$–$C_6$ alkylene or $C_1$–$C_6$ alkyleneoxy;

(iv) a group of the formula:

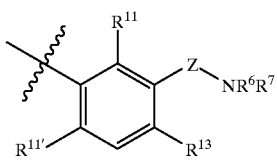

where Z, $R^6$, $R^7$, $R^{11}$, $R^{11'}$, and $R^{13}$ are as defined above;

(v) a group of the formula:

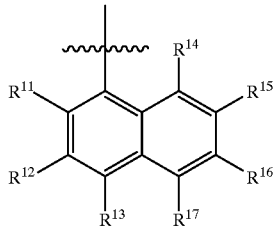

where $R^{11}$, $R^{12}$, and $R^{13}$ are as defined above, and $R^{14}$, $R^{15}$, $R^{16}$, and $R^{17}$ independently carry the same definitions as $R^{11}$; and (vi) a group of the formula:

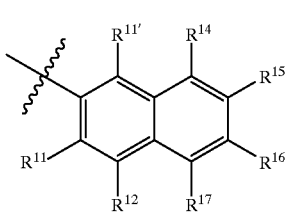

where $R^{11}$, $R^{11'}$, $R^{12}$, $R^{14}$, $R^{15}$, $R^{16}$, and $R^{17}$ are as defined above.

2. A compound or salt according to claim 1 of the formula:

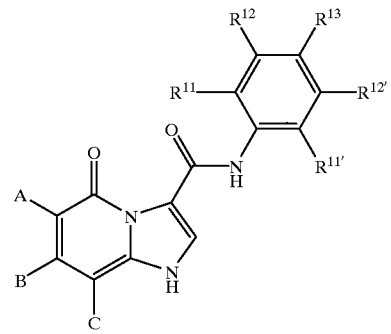

where A, B, C, $R^{11}$, $R^{11'}$, $R^{12}$, $R^{12'}$, and $R^{13}$ are as defined in claim 1.

3. A compound or salt according to claim 1 of the formula:

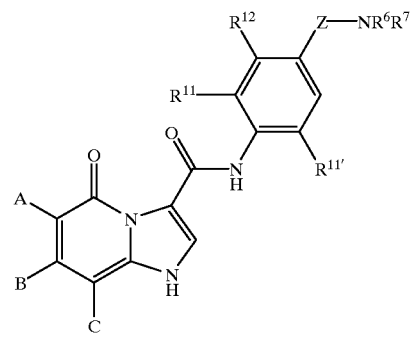

where A, B, C, $R^{11}$, $R^{11'}$, $R^{12}$, Z, $R^6$, and $R^7$ are as defined in claim 1.

4. A compound or salt according to claim 1 of the formula:

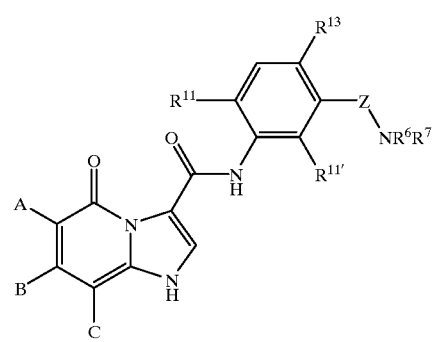

where A, B, C, $R^{11}$, $R^{11'}$, $R^{13}$, Z, $R^6$, and $R^7$ are as defined in claim 1.

5. A compound or salt according to claim 1 of the formula:

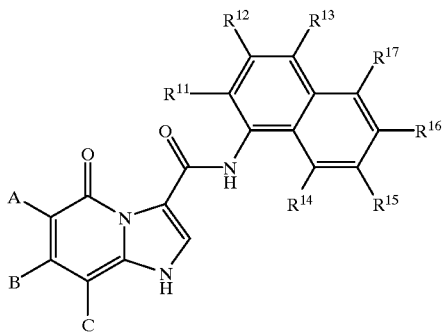

where A, B, C, $R^{11}$, $R^{12}$, $R^{13}$, $R^{14}$, $R^{15}$, $R^{16}$, and $R^{17}$ are as defined in claim 1.

6. A compound or salt according to claim 1 of the formula:

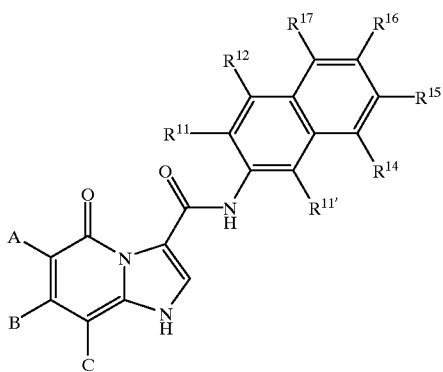

where A, B, C, $R^{11}$, $R^{12}$, $R^{11'}$, $R^{14}$, $R^{15}$, $R^{16}$, and $R^{17}$ are as defined in claim 1.

7. A compound or salt according to claim 1 of the formula:

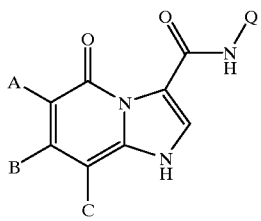

where A, B, C, and Q are as defined in claim 1.

8. A compound or salt according to claim 1 of the formula:

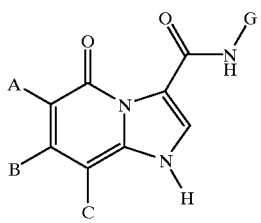

where A, B, C and G are as defined in claim 1.

9. A compound or salt according to claim 1 of the formula:

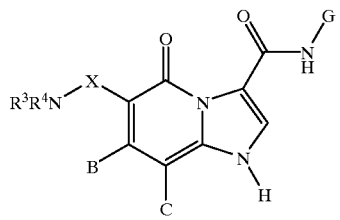

where $R^3$, $R^4$, B, C, and G are as defined in claim 1, and X is $C_1$–$C_6$ alkylene.

10. A compound or salt according to claim 1 of the formula:

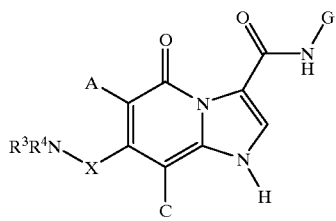

where $R^3$, $R^4$, A, C, and G are as defined in claim 1, and X is $C_1$–$C_6$ alkylene.

11. A compound or salt according to claim 1 of the formula of the formula:

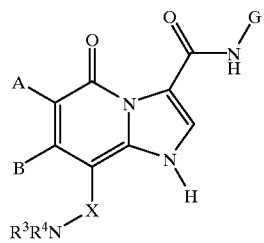

where $R^3$, $R^4$, A, B, and G are as defined in claim 1, and X is $C_1$–$C_6$ alkylene.

12. A compound or salt according to claim 1 of the formula:

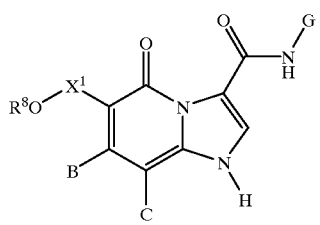

where B, C, and G are as defined in claim 1, $R^8$ is defined the same as $R^2$, and $X^1$ is $C_1$–$C_6$ alkylene or $C_1$–$C_6$ alkylene amino.

13. A compound or salt according to claim 1 of the formula:

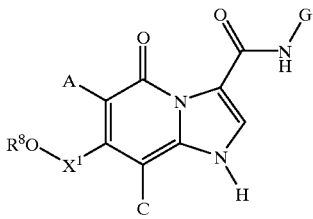

where A, C, and G are as defined in claim 1, $R^8$ is defined the same as $R^2$, and $X^1$ is $C_1$–$C_6$ alkylene or $C_1$–$C_6$ alkyleneamino.

14. A compound or salt according to claim 1 of the formula:

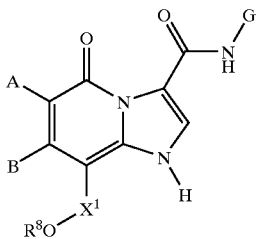

where A, B, and G are as defined in claim 1, $R^8$ is defined the same as $R^2$, and $X^1$ is $C_1$–$C_6$ alkylene or $C_1$–$C_6$ alkyleneamino.

15. A compound or salt according to claim 1 of the formula:

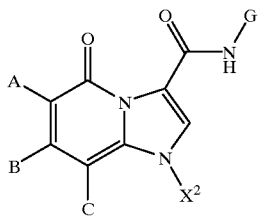

where A, B, C, G, are as defined in claim 1, and $X^2$ is $C_1$–$C_6$ alkyl.

16. A compound or salt according to claim 1 of the formula:

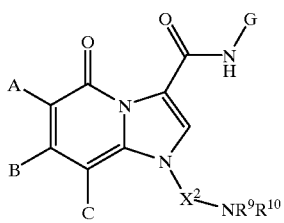

where A, B, C, and G are as defined in claim 1, $R^9$ and $R^{10}$ are independently defined the same as $R^3$ and $R^4$, and $X^2$ is $C_1$–$C_6$ alkylene.

17. A compound or salt according to claim 1 of the formula:

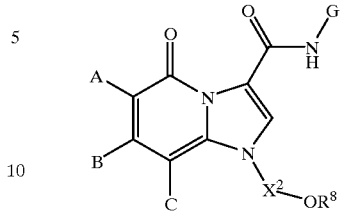

where A, B, C, G are as defined in claim 1, $R^8$ is defined the same as $R^2$, and $X^2$ is $C_1$–$C_6$ alkylene.

18. A compound or salt according to claim 1 of the formula:

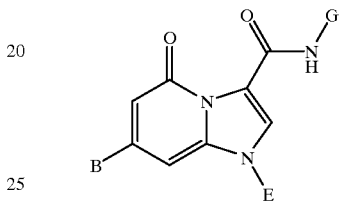

where E and G are as defined in claim 1 and B is selected from hydrogen and methyl.

19. A compound according to claim 1, which is N-(2,5-difluorophenyl) 7-methyl-5-oxo-imidazo[1,2-a]pyridyl-3-carboxamide or a pharmaceutically acceptable salt thereof.

20. A compound according to claim 1, which is N-Phenyl 5-oxo-imidazo[1,2-a]pyridine-3-carboxamide or a pharmaceutically acceptable salt thereof.

21. A compound according to claim 1, which is N-(2-Fluorophenyl) 5-oxo-imidazo[1,2-a]pyridine-3-carboxamide or a pharmaceutically acceptable salt thereof.

22. A compound according to claim 1, which is N-(2-fluoro 4-Chloro-phenyl) 5-oxo-imidazo [1,2-a]pyridine-3-carboxamide or a pharmaceutically acceptable salt thereof.

23. A compound according to claim 1, which is N-(2-Fluoro-3-trifluoromethylphenyl) 5-oxo-imidazo [1,2-a]pyridine-3-carboxamide or a pharmaceutically acceptable salt thereof.

24. A compound according to claim 1, which is N-(3-Methylphenyl) 5-oxo-imidazo[1,2-a]pyridine-3-carboxamide or a pharmaceutically acceptable salt thereof.

25. A compound according to claim 1, which is N-(4-Trifluoromethoxyphenyl) 5-oxo-imidazo[1,2-a]pyridine-3-carboxamide or a pharmaceutically acceptable salt thereof.

26. A compound according to claim 1, which is N-(2-Fluoro-4-ethoxyphenyl) 5-oxo-imidazo[1,2-a]pyridine-3-carboxamide or a pharmaceutically acceptable salt thereof.

27. A compound according to claim 1, which is N-(2-Fluoro-4-ethoxyphenyl) 5-oxo-imidazol[1,2-a]pyridine-3-carboxamide or a pharmaceutically acceptable salt thereof.

28. A compound according to claim 1, which is N-[4-(2-Dimethylaminoethoxy)phenyl] 5-oxo-imidazo[1,2-a]pyridine-3-carboxamide or a pharmaceutically acceptable salt thereof.

29. A compound according to claim 1, which is N-[4-(3-Imidazyl-1-propoxy)phenyl] 5-oxo-imidazo[1,2-a]pyridine-3-carboxamide hydrochloride or a pharmaceutically acceptable salt thereof.

30. A compound according to claim 1, which is N-(2-Naphthyl) 5-oxo-imidazo[1,2-a]pyridine-3-carboxamide or a pharmaceutically acceptable salt thereof.

31. A compound according to claim 1, which is N-Phenyl 7-methyl 5-oxo-imidazo[1,2-a]pyridine-3-carboxamide or a pharmaceutically acceptable salt thereof.

32. A compound according to claim 1, which is N-(4-Fluorophenyl) 7-methyl 5-oxo-imidazo[1,2-a]pyridine-3-carboxamide or a pharmaceutically acceptable salt thereof.

33. A compound according to claim 1, which is N-(4-Hydroxyphenyl) 7-methyl 5-oxo-imidazo[1,2-a]pyridine-3-carboxamide or a pharmaceutically acceptable salt thereof.

34. A compound according to claim 1, which is N-(2,4-Difluorophenyl) 7-methyl 5-oxo-imidazo[1,2-a]pyridine-3-carboxamide or a pharmaceutically acceptable salt thereof.

35. A compound according to claim 1, which is N-(2-Furoro-4-hydroxyphenyl) 7-methyl 5-oxo-imidazo[1,2-a]pyridine-3-carboxamide or a pharmaceutically acceptable salt thereof.

36. A compound according to claim 1, which is N-(4-Hydroxyphenyl) 1-(N-Ethyl) 7-methyl 5-oxo-imidazo[1,2-a]pyridine-3-carboxamide or a pharmaceutically acceptable salt thereof.

37. A pharmaceutical composition comprising a compound or salt according to claim 1 combined with at least one pharmaceutically acceptable carrier or excipient.

38. A package comprising a pharmaceutical composition of claim 37 in a container and further comprising indicia comprising at least one of:
   (a) instructions for using the composition to treat a patient suffering from an anxiety disorder, or
   (b) instructions for using the composition to treat a patient suffering from depression, or
   (c) instructions for using the composition to treat a patient suffering from a sleeping disorder.

39. A package comprising a pharmaceutical composition of claim 37 in a container and further comprising indicia comprising at least one of: instructions for using the composition to treat a patient suffering from Alzheimer's dementia or instructions for using the composition to enhance cognition in a patient.

* * * * *